United States Patent [19]
Fuller et al.

[11] Patent Number: 5,415,655
[45] Date of Patent: May 16, 1995

[54] MEDICAL DEVICE INCLUDING LIGHT ENERGY EMITTING CONTACT TIP WITH MEANS FOR RAISING TEMPERATURE OF THE TIP

[75] Inventors: Terry A. Fuller, Rydal; Mark A. DeStefano, Perkasie; Sanjeev Popli, Norristown; William C. Lawson, Willow Grove, all of Pa.

[73] Assignee: Surgical Laser Technologies, Inc., Oaks, Pa.

[21] Appl. No.: 233,475

[22] Filed: Apr. 26, 1994

Related U.S. Application Data

[63] Continuation of Ser. No. 874,247, Apr. 24, 1992, abandoned.

[51] Int. Cl.⁶ .............................................. A61N 5/06
[52] U.S. Cl. ........................................ 606/16; 606/11; 606/17
[58] Field of Search ..................... 606/2, 4, 11, 12, 15, 606/16, 17

[56] References Cited

U.S. PATENT DOCUMENTS

| | | |
|---|---|---|
| 4,592,353 | 4/1989 | Daikuzono . |
| 4,693,244 | 9/1987 | Daikuzono . |
| 4,695,697 | 2/1987 | Kosa ........................ 606/15 |
| 4,718,417 | 1/1988 | Kittrell et al. .................... 606/15 |
| 4,736,743 | 4/1988 | Daikuzono . |
| 4,832,024 | 5/1989 | Boussignac et al. .................. 606/15 |

FOREIGN PATENT DOCUMENTS

| | | |
|---|---|---|
| 64782/90 | 4/1991 | Australia . |
| PCT/JP89/0-1243 | 12/1989 | WIPO . |
| PCT/JP90/0-0040 | 9/1990 | WIPO . |
| PCT/JP90/0-1079 | 9/1990 | WIPO . |
| PCT/JP90/0-1122 | 9/1990 | WIPO . |

Primary Examiner—Stephen C. Pellegrino
Assistant Examiner—Sonya C. Harris
Attorney, Agent, or Firm—Seidel Gonda Lavorgna & Monaco

[57] ABSTRACT

A medical device has a flexible light guide having a light energy input end adapted for connection to a source of light energy and a light energy output end. The output end outputs a beam of light energy. The device includes a tip for contacting tissue to be treated by the device and irradiating the tissue with light energy. The tip consists essentially of light-transmissive material and has a working region for contacting and irradiating the tissue to be treated. The working region of the tip includes sidewalls. The tip has a bore therein for receiving the output end of the light guide. The output end of the light guide is at least partially surrounded by the light-transmissive material, and is positioned relative to the light-transmissive material so as to define an interface therebetween. The interface is in proximity to and in thermally-conductive relationship with the working region of the tip so that heat energy generated at the interface significantly raises the temperature of the tip's working region. The interface is sufficiently distant from the working region of the tip so as to allow at least a portion of the beam of light energy to strike the sidewalls at first locations, reflect back into the tip and exit the tip at second locations different from the first locations.

42 Claims, 4 Drawing Sheets

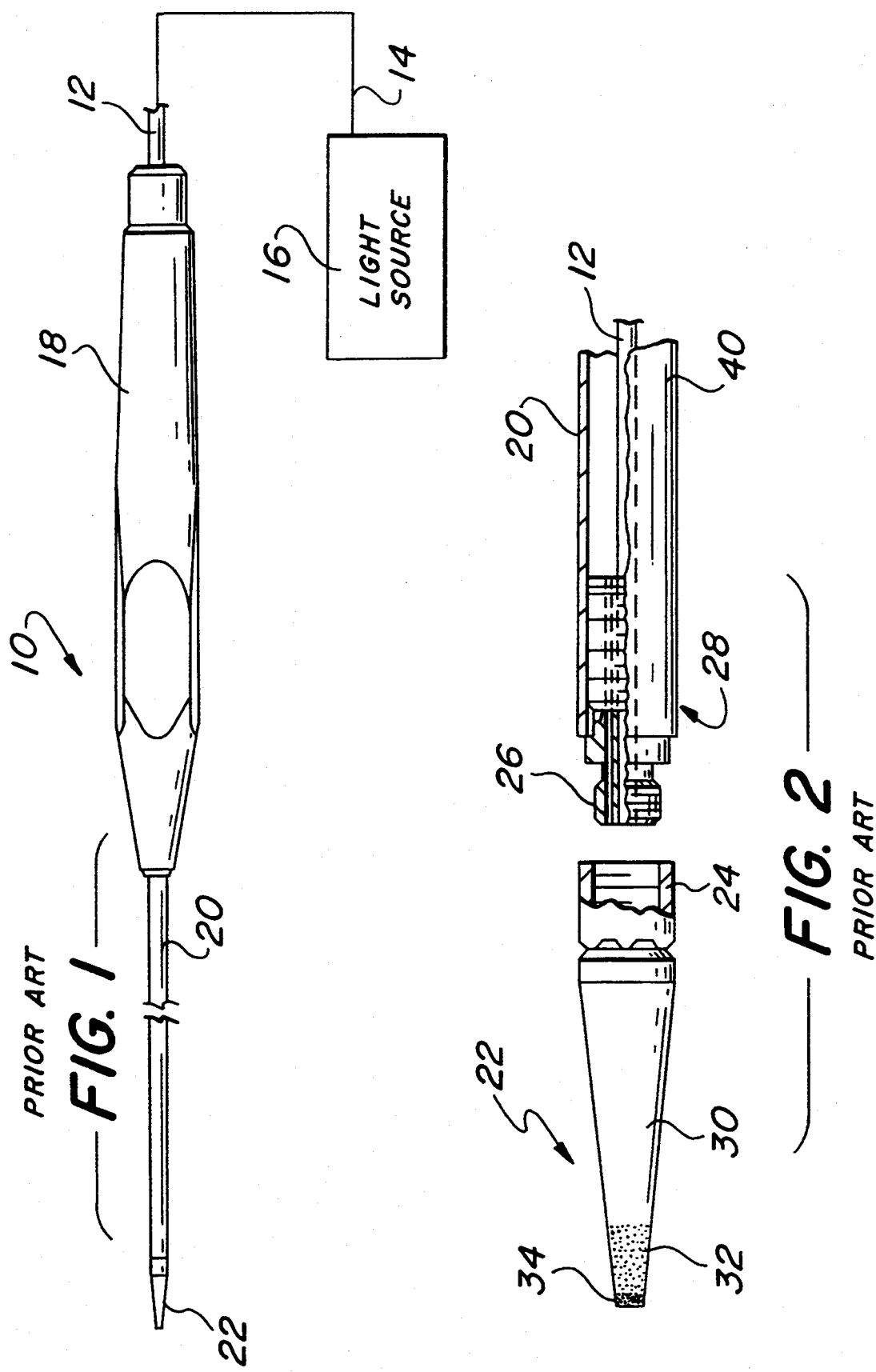

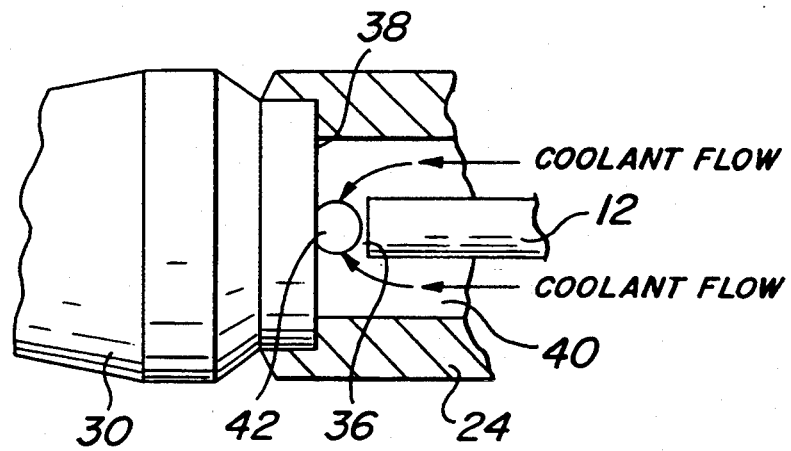
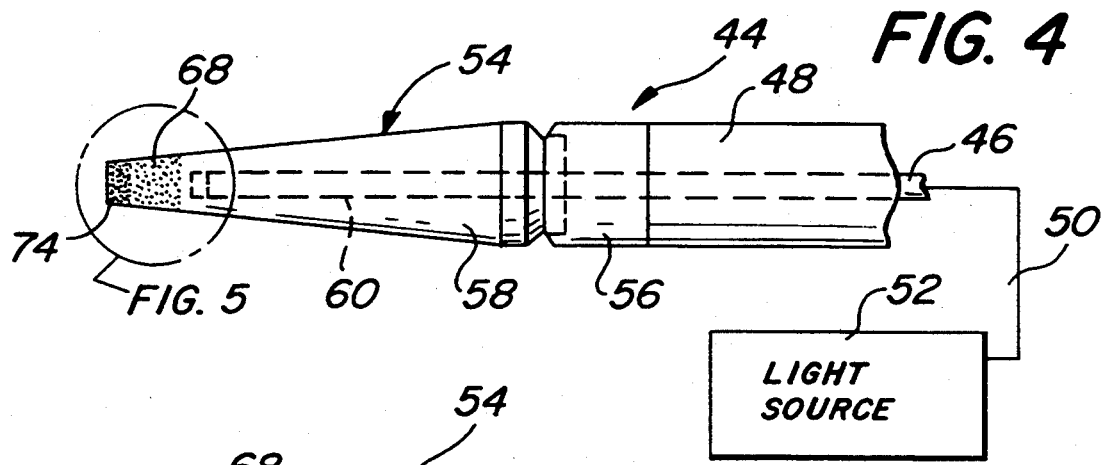
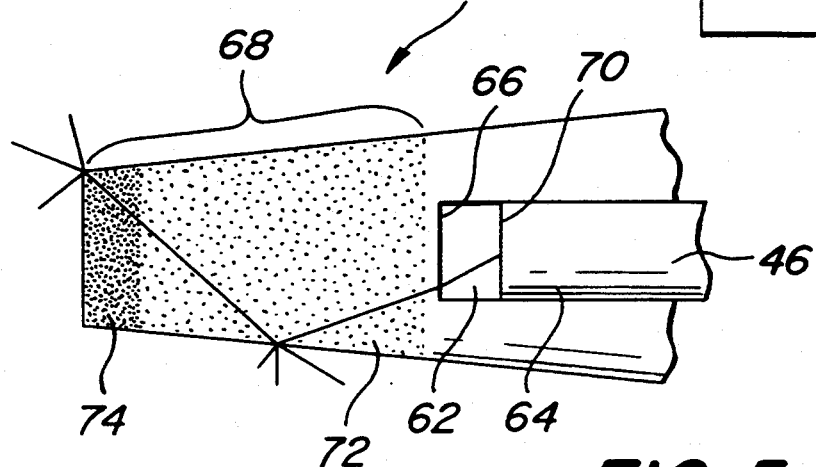

MEDICAL DEVICE INCLUDING LIGHT ENERGY EMITTING CONTACT TIP WITH MEANS FOR RAISING TEMPERATURE OF THE TIP

This is a continuation of application Ser. No. 07/874,247 filed on Apr. 24, 1992, now abandoned.

FIELD OF THE INVENTION

The present invention relates to medical devices for use in medicine and surgery in which the probe conveys light energy to tissue to be treated by the probe. The present invention is preferably used in a contact mode, in which the device directly contacts tissue to be treated. (As used herein, the term "treated" means exposed to light energy for any purpose, including but not limited to phototherapy, biostimulation, incision, vaporization, coagulation, and the like.)

BACKGROUND OF THE INVENTION

Light energy, including but by no means limited to laser light energy, has been used in medicine and surgery for many years. Different wavelengths of light interact differently with tissue, so tissue effects are wave-length-dependent. Lasers in particular are used in many different types of medical procedures. Different lasers cause different tissue effects, depending upon the wavelength of the laser emission. Among the types of lasers used in laser medicine are the $CO_2$ laser, the KTP laser and the neodymium:YAG laser.

Neodymium:YAG (Nd:YAG) lasers have been one of the most popular lasers in laser medicine. The Nd:YAG laser is an efficient and inexpensive source of high-power radiation in comparison to other types of lasers. Thus, cost-effective, high-power laser radiation can be made available at the treatment site. In addition, the absorption coefficient of water, the major constituent of tissue, is near its minimum at the fundamental wavelength (1.06 $\mu$m) of the radiation from Nd:YAG lasers. As a result, the radiation from an Nd:YAG laser penetrates deeply into tissue and is excellent for coagulation. Indeed, Nd:YAG lasers were initially used solely for coagulation. However, with suitably high power, laser radiation from Nd:YAG lasers can also be made to vaporize tissue.

In addition to laser light sources, which are referred to as "coherent," non-laser or "incoherent" light sources may also be used for medical and surgical procedures.

In order to get the light energy from the light source to the tissue to be treated, it is desirable to have a delivery system between the light source and the operative site. Such delivery systems as used in medicine and, in particular, in surgery can be broadly divided into those which either contact or do not contact tissue to be treated. In non-contact delivery systems, the distal end of the delivery system does not touch the tissue but, instead, uses a fiber optic or other light guide means to conduct light energy to a location adjacent, but not touching, the tissue. The light energy passes from the guide means through a gas or a liquid before reaching the tissue. The interface between the gas or liquid and the tissue can result in a substantial diffuse reflection of light energy (greater than 40% in some cases) away from the tissue.

To avoid this and other problems with non-contact procedures, techniques and devices have been developed in which the distal end of the delivery system comes into physical contact with the tissue. Direct physical contact between the distal end of the delivery system and the tissue substantially reduces energy losses due to reflection (typically to less than 5%). The reduction in diffuse reflection results in safer surgical procedures. The reduction in diffuse reflection results in less damage to adjacent tissues, and potentially less energy reflected into the surgeon's eyes. Contact procedures, by eliminating reflections, permit a more efficient use of light energy in surgery. Since energy loss is reduced, less power is required and, therefore, smaller, less expensive light sources or lasers can be used.

Contact delivery systems are disclosed in U.S. Pat. Nos. 4,592,353 and 4,693,244, both assigned to the assignee of the present invention.

U.S. Pat. No. 4,592,353 discloses a medical laser probe which has a contact member of laser transmitting material in front of a forward end of a fiber optic laser light guide so as to enable the probe to be used in contact with the tissue. There is a small gap between the forward end of the laser light guide and the rearward end of the contact member.

In the past, if a surgeon desired to use a large contact member for a particular procedure, it was necessary to use either a separate fiber optic and contact member, or a single large-diameter fiber optic with a shaped contact portion. In the first case, Fresnel loss results in a requirement for cooling the junction between the fiber optic and the contact member, and the resulting inefficiencies from the Fresnel loss led to undesirable power loss. In addition, the junction between the fiber optic and the contact member had to be kept well out of the surgical field to avoid burning adjacent tissues. In the second case, where a single fiber was used and the surgeon required a large contact area, the diameter of the contact portion was limited to the size of available fiber optics. This meant that the size of the contact portion was limited, or costly, non-standard, large diameter fibers running the entire distance between the laser source and the contact portion had to be used. In addition, such large diameter fibers are relatively inflexible.

U.S. Pat. No. 4,693,244 discloses another medical and surgical laser contact probe in which the portion of the probe that contacts tissue to be treated is tapered so as to emit laser radiation from the tip end face of the tapered portion substantially without leaking it out from the tapered portion. In one embodiment of the invention disclosed in U.S. Pat. No. 4,693,244, an artificial sapphire contact member is located in front of the forward end of a fiber optic, with a small gap between the forward end of the fiber optic and the contact member. (In another embodiment of the invention of the '244 patent, a single fiber optic is used to both convey laser energy from a laser source and contact tissue to be treated.)

When using two-piece contact delivery systems such as those described above, energy losses occur as the laser energy travels from the fiber optic through the gap on its way into the contact member. Losses occur from energy being reflected back toward the fiber. Such losses range from approximately 0.5 to 12% of the transmitted energy. The magnitude of such losses results in the need for a cooling medium to eliminate unwanted heating which occurs at the gap, where the reflected light energy is converted to heat energy. (These losses do not occur in the single-fiber embodiment of the invention of the '244 patent, since there is no gap.)

Hence, despite the advantages of prior devices for contact procedures, the prior two-piece contact devices still exhibit several shortcomings. Inefficiencies due to losses at the junction between the fiber optic and the contact member require higher power laser sources. Heat at the gap between the fiber optic and the contact member can result in temperatures sufficiently high to burn tissue and damage expensive surgical devices such as endoscopes in which the structure is placed, and can melt the mechanism holding the fiber and the contact member together and result in contact members separating from the device within a patient.

U.S. Pat. No. 4,592,353 recognizes this problem, and discloses cooling the laser probe with a cooling fluid, such as a liquid or a gas. This problem is also recognized by U.S. Pat. No. 4,832,024, which discloses a cooling system in the context of a cardiovascular catheter. In U.S. Pat. No. 4,832,024, coolant is recirculated and does not flow into the surgical field. The coolant in U.S. Pat. No. 4,592,353 is not recirculated, but instead flows into the surgical field. Thus, current methods of eliminating unwanted heat generated by losses at the junction between the optical fiber and the contact member involve the controlled use of coolant fluids which are caused to flow over the area in which the heat is generated. The fluid media are typically gases such as purified nitrogen or air, or liquids such as saline. The coolant fluid is then either allowed to escape out into the surgical field, or is recirculated and either recycled (returned to be re-used for cooling) or allowed to escape, but away from the surgical field. Existing cooling systems require pumps or other means for handling the cooling fluids. Such cooling systems add unnecessary cost in terms of materials and nursing labor to already-costly surgery. They also add to the required training of staff personnel and to the inventory of materials used for surgery. In addition, they are very inconvenient. Moreover, the choice of an inappropriate cooling medium can lead to catastrophic circumstances. If gas cooling is mistakenly utilized in a blood vessel or within a gas-sensitive organ, or if the wrong gas is utilized, severe patient injury or death can result. Even under the best of circumstances, the correct coolant can still cause problems, such as inadvertent cooling of the working region of the contact member by the fluid in the surgical field. Furthermore, coolant creates steep temperature gradients which may induce thermal shock.

Perhaps the greatest disadvantage of prior two-piece delivery system designs is that the heat loss at the gap between the fiber and the contact member is not useful for surgery. It is wasted energy from a costly energy source. It is known that increasing the temperature of the contact member results in elevated tissue temperatures, temperatures greater than would be created by the laser energy alone, which help vaporize the tissue. For example, U.S. Pat. No. 4,736,743, also assigned to the assignee of the present invention, discloses a medical laser probe in which the contact member, which contacts tissue is coated with a material which absorbs a portion of the laser radiation and converts it to heat. The combination of high contact member temperatures and laser radiation makes such coated devices highly effective for vaporizing tissue.

Prior laser probes have also been proposed in which the output end of a fiber optic is either embedded in, or spaced a short distance from, a transmissive contact member. For example, PCT publications PCT/JP90/01122 and PCT/JP90/01079 show such probes. However, neither of those publications recognizes or deals with the issue of heat generated at the interface between the fiber optic and the contact member, and neither of those publications makes any suggestion that such heat can be put to practical use. Indeed, those publications teach away from the concept of using the heat generated at the interface by keeping the interface well away from the working region of the tip, so that the heat can be dissipated by the tip material before it can be used at the working region.

The present invention is based in part on the realization that heat generated at the interface between the fiber optic and the contact member can be used to enhance the therapeutic effect of a contact member by putting otherwise wasted energy to use in raising the temperature of the contact member.

SUMMARY OF THE INVENTION

The present invention is broadly directed to a medical device comprising flexible light guide means having a light energy input end adapted for connection to a source of light energy and a light energy output end. The device includes tip means for contacting tissue to be treated by the device and for irradiating said tissue with light energy. The tip means consists essentially of light-transmissive material and has a working region for contacting and irradiating the tissue to be treated. The tip means has a recess therein for receiving the output end of the light guide means. The output end of the light guide means is at least partially surrounded by the light-transmissive material, and is positioned relative to the light-transmissive material so as to define an interface therebetween. The interface is in proximity to and in thermally-conductive relationship with the working region of the tip means.

The present invention also includes a medical probe for use in medical procedures in which at least a portion of the probe is intended to contact tissue to be treated thereby, comprising optical fiber means having a light energy input end and a light energy output end, said input end being adapted for connection to a source of light energy, and tip means consisting essentially of light-transmissive material and having a working region adapted to contact tissue to be treated, said tip means having a recess therein for receiving said output end of said optical fiber means, said output end being at least partially surrounded by said light-transmissive material, said output end of said optical fiber being spaced from said light-transmissive material so as to define a gap therebetween, said gap being in proximity to and in thermally-conductive relationship with said working region of said tip means.

The invention further includes a contact tip for a medical device, said tip consisting essentially of a light-transmissive material and comprising a light energy emitting working region for contacting tissue to be treated by said device and recess means for receiving therein an output end of a light guide means for conducting light energy from a source thereof to said tip, said recess defining an interface between said output end of said light guide means and said light-transmissive material, said interface being in proximity to and in thermally-conductive relation with said working region.

Still further, the invention includes a contact delivery system for laser medicine, comprising a source of laser radiation, optical fiber means having a laser radiation input end and a laser radiation output end, said input end being in laser radiation receiving relationship to said source of laser radiation, support means for supporting and manipulating said optical fiber means, and tip means adjacent said laser radiation output end of said optical fiber means in laser radiation receiving relationship to said output end, said tip means consisting essentially of laser radiation transmissive material and having a working region adapted to contact tissue to be treated, said tip means having a recess therein for receiving said output end of said optical fiber means, said output end being at least partially surrounded by said laser radiation transmissive material, said output end of said optical fiber being spaced from said laser radiation transmissive material so as to define a gap therebetween, said gap being in proximity to and in thermally-conductive relationship with said working region of said tip means.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 1 is a simplified sketch of a medical probe according to the prior art.

FIG. 2 is an enlarged view of a portion of FIG. 1, showing the assembly of a medical device according to the prior art.

FIG. 3 is an enlarged partial view of the interface between the tip and the fiber optic according to the prior art.

FIG. 4 is a simplified sketch of a medical device according to the present invention.

FIG. 5 is an enlarged view of the working region of the medical device shown in FIG. 4.

DESCRIPTION OF THE INVENTION

Figure 6A:
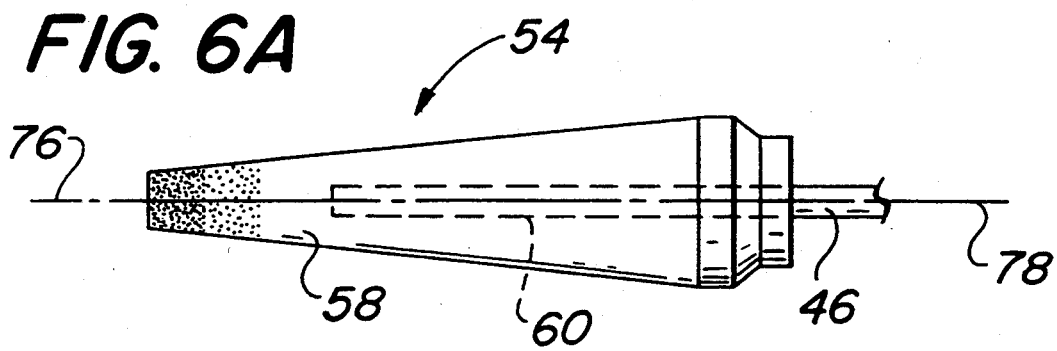
FIGS. 6A, 6B and 6C are simplified depictions of several alternate embodiments of the present invention.

Referring now to the drawings, wherein like numerals indicate like elements, there is shown in FIG. 1 a medical probe 10 according to the prior art. Prior art probe 10 comprises a light guide 12, having an input end 14 connected to a source 16 of light energy. Light source 16 is preferably, but not necessarily, a laser light source. In addition to laser light sources, which are referred to as "coherent," non-laser or "incoherent" light sources may be used.

Light guide 12 may be a flexible fiber optic or other optical waveguide. Where light guide 12 is a fiber optic, the fiber optic is typically, but not necessarily, quartz, although any suitable material may be used for the light guide. Light guide 12 extends through a handpiece 18, by means of which a surgeon can manipulate probe 10. Handpiece 18 includes a wand 20. Wand 20 is typically a thin-walled tube which supports light guide 12 and enables prior art probe 10 to be manipulated. At the distal end of prior art probe 10 is a contact member, or tip, 22, which is removably attached to wand 20, such as by a threaded hub 24. As best seen in FIG. 2, threaded hub 24 threadedly engages a threaded member 26 at the distal end 28 of wand 20. Light guide 12 extends through wand 20 and threaded member 26, and terminates at a distal end substantially flush with the distal end of threaded member 26. As will be understood, light guide 12 guides light energy from light source 16 to tip 22.

Tip 22 consists essentially of a light-transmissive portion 30, which may have any desired shape. For example, as shown in the figures, transmissive portion 30 may be conical. For purposes of this invention, the term "light-transmissive" includes materials which are optically clear, translucent and/or light-scattering or light-diffusing materials. In addition, if desired, the working region 32 of tip 22 (i.e., the region of tip 22 intended to contact the tissue), may optionally have a surface treatment 34, such as for example an energy-absorbing coating or an energy-diffusing surface.

When tip 22 is assembled to wand 20, there is a small gap between the distal end, or output end, 36 of light guide 12 and the input end 38 of the light transmissive material 30, as seen in FIG. 3. It is at this gap, or interface, that Fresnel losses and consequent heating occur as light energy from the output end 36 of light guide 12 travels across the gap and into tip 22. To control the heating, prior art probe 10 is typically provided with a coolant flow channel 40 within wand 20 and hub 24, which surrounds light guide 12. A fluid coolant, such as gas or air, is made to flow through coolant flow channel 40 from an upstream location at or near hand piece 18, through wand 20 through hub 24, and into the gap between output end 36 of light guide 12 and input end 38 of light transmissive portion 30. The coolant fluid absorbs the heat generated by the Fresnel losses, and escapes through coolant escape opening 42 into the surgical field.

Referring now to FIGS. 4 and 5, there is shown a medical device according to the present invention, in the form of a probe 44. Probe 44 comprises a light guide 46 which may be supported by a wand 48. As in the prior art, light guide 46 may be a fiber optic. A first end 50 of light guide 46 is connected to a light source 52, such as a laser, in the same manner as prior art probe 10 illustrated in FIG. 1. It should be understood that the present invention, although described as used in conjunction with a laser light source for purposes of illustrating the invention, is applicable to both laser (coherent) and non-laser (incoherent) light sources. Thus, the invention is usable with any type of light source and is not limited to laser medical procedures. In addition, the term "light energy" as used herein is understood to include both coherent and incoherent light, and also includes energy throughout what is typically referred to as the optical portion of the electromagnetic spectrum, from infrared through ultraviolet.

Although a probe comprising a handpiece is illustrated as the context of the present invention, it should be understood that the present invention is not limited solely to medical instruments having a handpiece. Rather, the invention is applicable to all manner of medical instruments, such as those that may be used with endoscopes, catheters, and so forth, as well as to procedures in which the probe alone forms the instrument, such as procedures in which the probe alone is inserted into a blood vessel, for example.

A tip 54 is attached to the distal end of wand 48, such as by a threaded hub 56, in the same manner as tip 22 is attached to wand 20 of prior art probe 10. As with prior art tip 22, tip 54 includes a light transmissive portion 58, which may have any desired shape. For example, as shown in the figures, transmissive portion 58 may be conical. However, other shapes, such as rounded, hemispherical, curved, bent, hooked or other shapes, may also be employed. In addition, if desired, the working region 68 of tip 54 (the region of tip 54 intended to contact the tissue), may optionally have a surface treatment 74, such as for example an energy-absorbing coating or an energy-diffusing surface. For purposes of this invention, the term "light-transmissive" includes materials which are optically clear, translucent and/or light-scattering or light-diffusing materials. Light transmissive portion 58 is preferably sapphire (i.e., aluminum oxide, or $Al_2O_3$), either single crystal or polycrystalline, but may be made of other suitable materials. The choice of material depends upon the desired tissue effect to be achieved. Sapphire is preferred because it is physiologically neutral, has high mechanical strength, high hardness, high light transmission, excellent temperature stability and high thermal conductivity, and exhibits low tissue adhesion. Artificial sapphire, or other materials such as quartz or zinc selenide (ZnSe), for example, may also be used without departing from the invention.

Unlike probes according to the prior art, where light guide 12 terminates substantially flush with the distal end of wand 20, in the present invention light guide 46 extends beyond the distal end of wand 48 into a recess, or bore, 60 in light transmissive portion 58. Bore 60 is preferably coaxial with light guide 46, and has a diameter just slightly greater than the outer diameter of light guide 46, so that there is a snug but non-binding fit between light guide 46 and light transmissive portion 58.

As shown in FIG. 5, a small gap 62 may be left at the interface between the distal end 64 of light guide 46 and the input surface 66 of light transmissive portion 58. Gap 62 is located in proximity to and in thermally-conductive relation to working region 68 of tip 54. The spacing between the distal end 64 of light guide 46 to the input surface 66 of light transmissive portion 58 is preferably within the range from 0.005 through 0.040 inches. Greater or lesser distances, or even direct contact between distal end 64 and input surface 66, i.e., a "zero spacing" structure, will also work. It should be understood that, even with direct contact between distal end 64 and input surface 66, inevitable surface imperfections may result in small spaces between distal end 64 and input surface 66. However, the presence of such small spaces is deemed not to detract from the behavior of the invention when "zero spacing" is employed. A gap 62 is preferred over "zero spacing," however, because it is believed to improve the integrity of the junction by permitting tip 54 to be used at high powers.

In addition, the dimensions of bore 60 can be varied from the fiber diameter to any larger size not exceeding the mechanical stability of tip 54. For example, a thin walled, hollow structure can be used, consistent with the necessary mechanical strength required of tip 54.

If desired, light guide 46 and tip 54 may be permanently affixed together, such as by the use of a suitable adhesive between the outer surface of light guide 46 and the inner surface of bore 60, or by fusing light guide 46 and tip 54 together, such as by heat fusion. Alternatively, mechanical means, such as crimping hub 56 to wand 48, may be employed.

Tip 54 may, as noted above in connection with tip 22, be substantially transparent, or may be translucent, light-scattering and/or light-diffusing. In addition, tip 52 may be any combination of transparent, translucent, light-scattering or light-diffusing materials, without departing from the scope of the present invention.

In operation, light energy from light source 52 is transmitted along light guide 46 until it reaches the distal, or output, end 64, where it is emitted from the light guide/gap interface 70. A typical emitted ray 72 is illustrated in FIG. 5. Some energy from ray 72 is lost at interface 70 due to Fresnel losses, which are inherent at any interface between one optical medium and another. After being emitted from light guide 46, ray 72 propagates across gap 62 until it reaches input surface 66, where it enters the transmissive portion 58 of tip 54. Ray 72 loses more energy at the interface between gap 62 and input surface 66, again due to Fresnel losses.

The Fresnel losses and subsequent absorption which occur at these interfaces result in heat being generated in the small gap 62. By locating gap 62 near and in thermally-conductive relation to the working region 68 of tip 54, the heat generated in gap 62 by the Fresnel losses raises the temperature of the light transmissive portion 58 in the vicinity of working region 68. The heat due to Fresnel losses, which heretofore was simply waste heat, is now utilized to increase the temperature of working region 68. If desired, in order to increase the temperature of working region 68 still further, a laser energy absorbing coating 74 may be applied to working region 68.

It will be appreciated that the present invention makes it possible to relocate the light guide/tip junction from outside the desired working region of the tip to a location near, or in proximity to, the working region. Hence, energy which previously would have been lost through reflection away from the working region and carried off by coolant is instead utilized constructively within the tip to increase its temperature. This eliminates the need for a coolant system and, therefore, eliminates the concomitant requirement that a physician must determine the most beneficial or safest method of cooling the tip during the surgical procedure to be performed. The present invention also lowers the cost of laser surgical procedures by eliminating coolant pumps and associated coolant materials and permitting the use of a less expensive fiber delivery systems, that is, those which do not require coolant flow channels to carry coolant fluid.

Figure 6B:
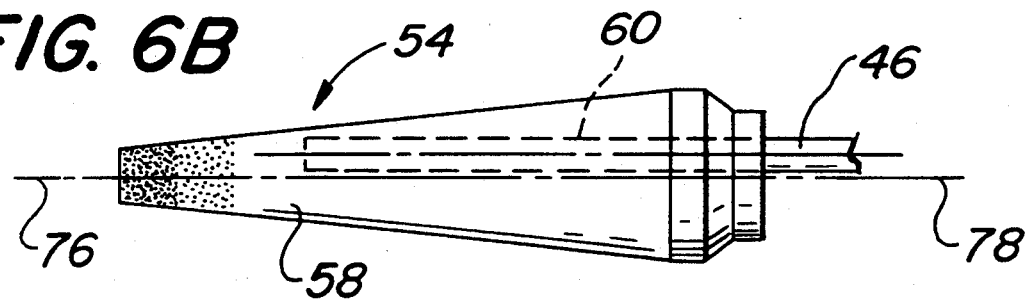
Figure 6C:
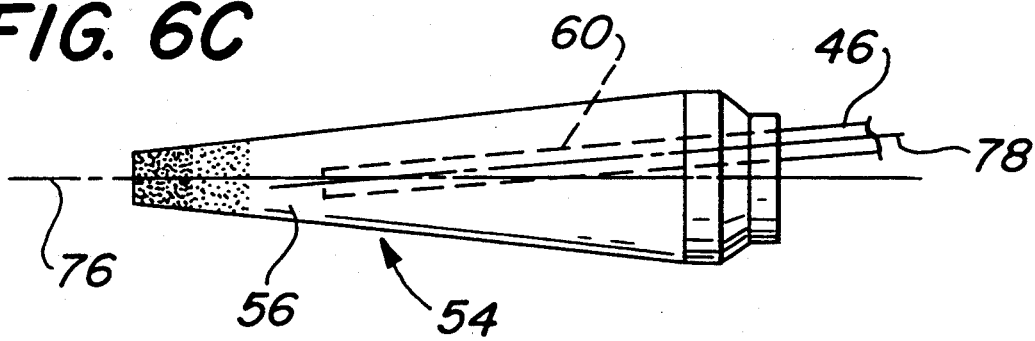

Variations of the structure already illustrated and described are possible without departing from the present invention. For example, the axis 76 of tip 54 and the axis 78 of light guide 46 may be the same, as shown in FIG. 6A, or they may be different. Tip axis 76 may be parallel to and spaced apart from axis 78 of light guide 46, as shown in FIG. 6B, or tip axis 76 and axis 78 of light guide 46 may intersect at a point X, as shown in FIG. 6C. Tip axis 76 and axis 78 of light guide 46 need not be in the same plane, but may be skew, i.e., neither parallel nor intersecting, although such a configuration has been omitted from the drawings for the sake of clarity.

Figure 8:
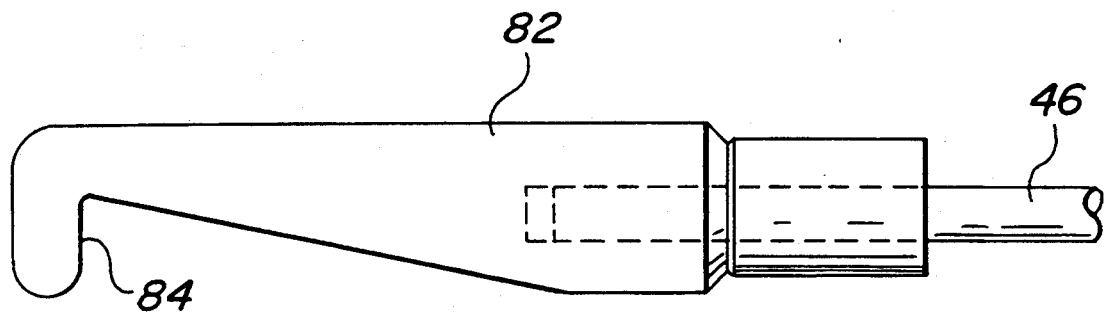
FIGS. 8 and 9 illustrate different tip shapes within the scope of the present invention.

Variations in the shape of the tip are also included within the scope of the present invention. For example, FIG. 8 illustrates a tip 82 which has a hook shape. The working region of tip 82 is indicated by reference numeral 84. Preferably, the surface of working region 84 is coated with an energy-absorbing coating which absorbs at least some of the light energy emitted from the working region. The shape of tip 82 is useful in certain procedures where it is desired to sever a blood vessel, for example, without bleeding from the ends of the vessel.

Figure 9:
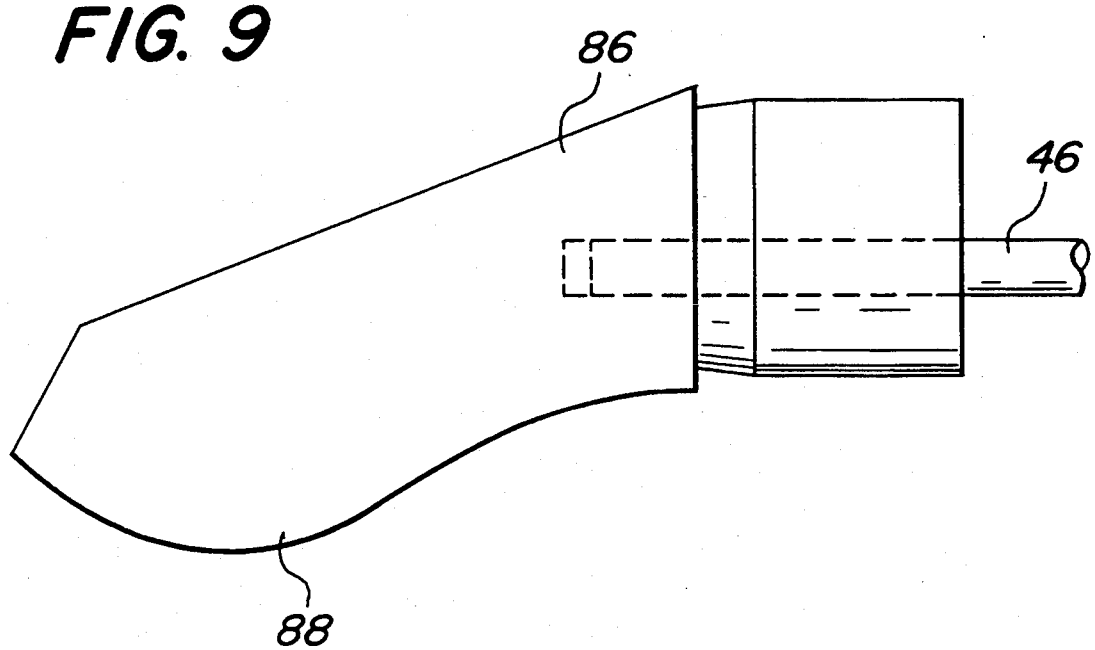

FIG. 9 illustrates a tip 86 which is angled. The working region 88 is curved in shape, and preferably is a portion of a sphere. Such a shape emits light energy over a broader area than a conical tip, such as tip 54, for example. As with the other tips illustrated and described, tip 86 may have a surface treatment on the surface of working region 88, such as an energy-absorbing or an energy-diffusing coating.

Figure 7:
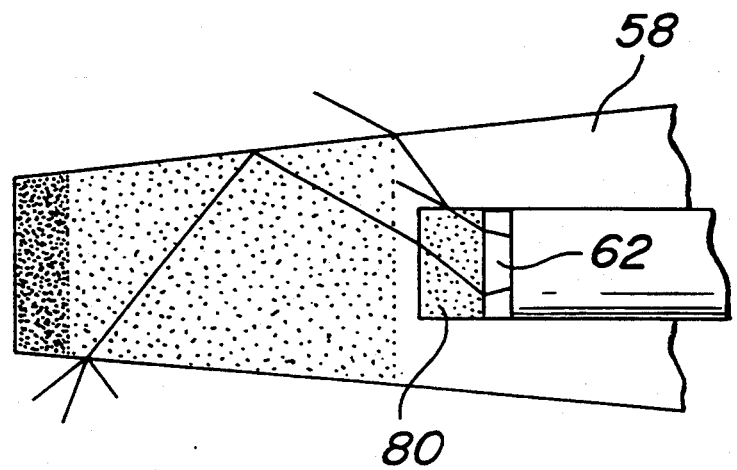
FIG. 7 is an enlarged view of the working region of the medical device of the present invention, illustrating another alternate embodiment of the invention.

In addition, gap 62 may be left empty, or may include therein a medium 80 as illustrated in FIG. 7. Medium 80 can fill the entire gap 62, or only a portion of the gap 62, as illustrated in FIG. 7. Medium 80 may be any suitable scattering or diffusing material, such as but not limited to a porous sapphire having voids or a sapphire having inclusions therein, or may be a material which both scatters and partially absorbs light. If medium 80 is a light scattering material, it may be of any index of refraction, either the same as or different from the index of refraction of the tip material. In addition, medium 80 may be an optically clear material which has a refractive index different from the refractive index of the tip 54.

The present invention may be embodied in other specific forms without departing from the spirit or essential attributes thereof and, accordingly, reference should be made to the appended claims, rather than to the foregoing specification, as indicating the scope of the invention.

We claim:

1. A medical device, comprising a flexible light guide having a light energy input end and a light energy output end from which light energy input into the light guide input end exits as a beam of light energy, said input end being adapted for connection to a source of light energy, and a tip for contacting tissue to be treated by said device and for irradiating said tissue with light energy, said tip consisting essentially of light-transmissive material and having a working region for contacting and irradiating said tissue to be treated, the working region of the tip including sidewalls, said tip having a bore therein for receiving said output end of said light guide, said output end being at least partially surrounded by said light-transmissive material, said output end of said light guide being positioned relative to said light-transmissive material so as to define an interface therebetween, said interface being in proximity to and in thermally conductive relationship with said working region of said tip so that heat energy generated at the interface significantly raises the temperature of the working region of said tip, said interface being sufficiently distant from the working region of said tip so as to allow at least a portion of the beam of light energy to strike the sidewalls at first locations, reflect back into the tip and exit the tip at second locations different from the first locations.

2. A medical device as in claim 1, wherein the light source is a laser.

3. A medical device as in claim 1, wherein the light source is a source of incoherent light.

4. A medical device as in either claim 1, wherein the light-transmissive material is aluminum oxide.

5. A medical device as in claim 4, wherein the aluminum oxide is a single crystalline form.

6. A medical device as in claim 1, wherein said light transmissive material is substantially transparent.

7. A medical device as in claim 1, wherein said light guide comprises an optical fiber.

8. A medical probe for use in medical procedures in which at least a portion of the probe is intended to contact tissue to be treated thereby, comprising an optical fiber having a light energy input end and a light energy output end, said input end being adapted for connection to a source of light energy, the light energy input thereto exiting the output end as a beam of light energy, and a tip consisting essentially of light-transmissive material and having a working region adapted to contact tissue to be treated, the working region of the tip including sidewalls, said tip having a bore therein for receiving said output end of said optical fiber, said output end being at least partially surrounded by said light-transmissive material, said output end of said optical fiber being spaced from said light-transmissive material so as to define a gap therebetween, said gap being in proximity to and in thermally-conductive relationship with said working region of said tip so that heat energy generated at the gap significantly raises the temperature of the working region of said tip, said gap being sufficiently distant from the working region of said tip so as to allow at least a portion of the beam of light energy to strike the sidewalls at first locations, reflect back into the tip and exit the tip at second locations different from the first locations.

9. A medical probe as in claim 8, wherein the light source is a laser.

10. A medical probe as in claim 8, wherein the light source is a source of incoherent light.

11. A medical probe as in claim 8, wherein the light-transmissive material is aluminum oxide.

12. A medical probe as in claim 11, wherein the aluminum oxide is a single crystalline form.

13. A medical probe as in claim 8, wherein the light transmissive material is substantially transparent.

14. A medical probe as in claim 8, where the light transmissive material is at least partially translucent.

15. A medical laser probe for use in laser medicine in which at least a portion of the probe is intended to contact tissue to be treated thereby, comprising an optical fiber having a laser radiation input end and a laser radiation output end, said input end being adapted for connection to a source of laser radiation, the laser radiation input thereto exiting the output end as a beam of laser radiation, and a tip consisting essentially of laser radiation transmissive material and having a working region adapted to contact tissue to be treated, the working region of the tip including sidewalls, said tip having a bore therein for receiving said output end of said optical fiber, said output end being at least partially surrounded by said laser radiation transmissive material, said output end of said optical fiber being spaced from said laser radiation transmissive material so as to define a gap therebetween, said gap being in proximity to and in thermally-conductive relationship with said working region of said tip so that heat energy generated at the gap significantly raises the temperature of the working region of said tip, said gap being sufficiently distant from the working region of said tip so as to allow at least a portion of the beam of laser radiation to strike the sidewalls at first locations, reflect back into the tip and exit the tip at second locations different from the first locations.

16. A medical laser probe as in claim 15, wherein at least a portion of said optical fiber means extends through a wand for supporting and permitting manipulation of said probe.

17. A medical laser probe as in claim 15, wherein said laser radiation transmissive material is aluminum oxide.

18. A medical laser probe as in claim 17, wherein the aluminum oxide is a single crystalline form.

19. A medical laser probe as in claim 15, wherein said tip has a substantially conical shape.

20. A medical laser probe as in claim 15, further comprising a surface treatment on said working region for absorbing a portion of said laser radiation emitted from said working region and converting said portion of laser radiation to heat energy.

21. A medical laser probe as in claim 15, wherein said gap contains gas.

22. A medical laser probe as in claim 15, wherein said gap contains a light-scattering material.

23. A medical laser probe as in claim 15, wherein the spacing between the output end of said optical fiber and said laser radiation transmissive material is substantially zero.

24. A medical laser probe for use in laser medicine in which at least a portion of the probe is intended to contact tissue to be treated thereby, comprising an optical fiber having a laser radiation input end and a laser radiation output end, said input end being adapted for connection to a source of laser radiation, the laser radiation input thereto exiting the output end of the optical fiber as a beam of laser radiation, and a tip consisting essentially of laser transmissive aluminum oxide and having a working region adapted to contact tissue to be treated, the working region of the tip including sidewalls, said tip having a bore therein for receiving said output end of said optical fiber, said output end being at least partially surrounded by said laser radiation transmissive material, said output end of said optical fiber being spaced from said laser radiation transmissive material so as to define a gap therebetween, said gap being in proximity to and in thermally-conductive relationship with said working region of said tip so that heat energy generated at the gap significantly raises the temperature of the working region of said tip, said gap being sufficiently distant from the working region of said tip so as to allow at least a portion of the beam of laser radiation to strike the sidewalls at first locations, reflect back into the tip and exit the tip at second locations different from the first locations.

25. A medical laser probe as in claim 24, wherein said aluminum oxide is a single crystalline form.

26. A contact delivery system for laser medicine, comprising a source of laser radiation, an optical fiber having a laser radiation input end and a laser radiation output end, said input end being in laser radiation receiving relationship to said source of laser radiation, the laser radiation input thereto exiting the output end as a beam of laser radiation, a support for supporting and manipulating said optical fiber, and a tip adjacent said laser radiation output end of said optical fiber in laser radiation receiving relationship to said output end, said tip consisting essentially of laser radiation transmissive material and having a working region adapted to contact tissue to be treated, the working region of the tip including sidewalls, said tip having a bore therein for receiving said output end of said optical fiber, said output end being at least partially surrounded by said laser radiation transmissive material, said output end of said optical fiber being spaced from said laser radiation transmissive material so as to define a gap therebetween, said gap being in proximity to and in thermally-conductive relationship with said working region of said tip so that heat energy generated at the gap significantly raises the temperature of the working region of said tip, said gap being sufficiently distant from the working region of said tip so as to allow at least a portion of the beam of laser radiation to strike the sidewalls at first locations, reflect back into the tip and exit the tip at second locations different from the first locations.

27. A contact delivery system as in claim 26, wherein said laser radiation transmissive material is aluminum oxide.

28. A contact delivery system as in claim 27, wherein said aluminum oxide is a single crystalline form.

29. A contact tip for a medical device, said tip consisting essentially of a light-transmissive material and comprising a light energy emitting working region for contacting tissue to be treated by said device and a bore for receiving therein an output end of a light guide for conducting light energy from a source thereof to said tip, the light energy input thereto exiting the output end of the light guide as a beam of light energy, the working region of the tip including sidewalls, said bore defining an interface between said output end of said light guide and said light-transmissive material, said interface being in proximity to and in thermally-conductive relation with said working region so that heat energy generated at the interface significantly raises the temperature of the working region of said tip, said interface being sufficiently distant from the working region of said tip so as to allow at least a portion of the beam of light energy to strike the sidewalls at first locations, reflect back into the tip and exit the tip at second locations different from the first locations.

30. A tip as in claim 29, wherein said light transmissive material is aluminum oxide.

31. A tip as in claim 30, wherein said aluminum oxide is a single crystalline form.

32. A tip as in claim 29, wherein said tip is substantially conical in shape.

33. A tip as in claim 29, wherein said working region includes a surface treatment.

34. A tip as in claim 33, wherein said surface treatment absorbs a portion of light energy emitted from working region.

35. A tip as in claim 33, wherein said surface treatment diffuses light energy emitted from said working region.

36. A tip as in claim 29, wherein said light guide is an optical fiber.

37. A tip as in claim 29, wherein the source of light energy is a laser.

38. A tip as in claim 29, wherein said interface is a gap.

39. A medical laser probe for use in laser medicine in conjunction with use of an endoscope in which at least a portion of the probe is intended to contact tissue to be treated thereby, comprising an optical fiber having a laser radiation input end and a laser radiation output end, said input end being adapted for connection to a source of laser radiation, the laser radiation input thereto exiting the output end as a beam of laser radiation, and a tip consisting essentially of laser radiation transmissive material and having a working region adapted to contact tissue to be treated, the working region of the tip including sidewalls, said tip having a bore therein for receiving said output end of said optical fiber, said output end being at least partially surrounded by said laser radiation transmissive material, said output end of said optical fiber being spaced from said laser radiation transmissive material so as to define a gap therebetween, said gap being in proximity to and in thermally-conductive relationship with said working region of said tip so that heat energy generated at the gap significantly raises the temperature of the working region of said tip, said gap being sufficiently distant from the working region of said tip so as to allow at least a portion of the beam of laser radiation to strike the sidewalls at first locations, reflect back into the tip and exit the tip at second locations different from the first locations.

40. A contact delivery system for laser medicine in conjunction with use of an endoscope, comprising a source of laser radiation, an optical fiber having a laser radiation input end and a laser radiation output end, said input end being in laser radiation receiving relationship to said source of laser radiation, the laser radiation input thereto exiting the output end as a beam of laser radiation, a support for supporting and manipulating said optical fiber, and a tip adjacent said laser radiation output end of said optical fiber in laser radiation receiving relationship to said output end, said tip consisting essentially of laser radiation transmissive material and having a working region adapted to contact tissue to be treated, the working region of the tip including sidewalls, said tip having a bore therein for receiving said output end of said optical fiber, said output end being at least partially surrounded by said laser radiation transmissive material, said output end of said optical fiber being spaced from said laser radiation transmissive material so as to define a gap therebetween, said gap being in proximity to and in thermally-conductive relationship with said working region of said tip so that heat energy generated at the gap significantly raises the temperature of the working region of said tip, said gap being sufficiently distant from the working region of said tip so as to allow at least a portion of the beam of laser radiation to strike the sidewalls at first locations, reflect back into the tip and exit the tip at second locations different from the first locations.

41. A medical laser probe for use with a handpiece in laser medicine in which at least a portion of the probe is intended to contact tissue to be treated thereby, comprising an optical fiber having a laser radiation input end and a laser radiation output end, said input end being adapted for connection to a source of laser radiation, the laser radiation input thereto exiting the output end as a beam of laser radiation, and a tip consisting essentially of laser radiation transmissive material and having a working region adapted to contact tissue to be treated, the working region of the tip including sidewalls, said tip having a bore therein for receiving said output end of said optical fiber, said output end being at least partially surrounded by said laser radiation transmissive material, said output end of said optical fiber being spaced from said laser radiation transmissive material so as to define a gap therebetween, said gap being in proximity to and in thermally-conductive relationship with said working region of said tip so that heat energy generated at the gap significantly raises the temperature of the working region of said tip, said gap being sufficiently distant from the working region of said tip so as to allow at least a portion of the beam of laser radiation to strike the sidewalls at first locations, reflect back into the tip and exit the tip at second locations different from the first locations.

42. A contact delivery system for laser medicine for use with a handpiece, comprising a source of laser radiation, an optical fiber having a laser radiation input end and a laser radiation output end, said input end being in laser radiation receiving relationship to said source of laser radiation, the laser energy input thereto exiting the output end as a beam of laser radiation, a support for supporting and manipulating said optical fiber, and a tip adjacent said laser radiation output end of said optical fiber in laser radiation receiving relationship to said output end, said tip consisting essentially of laser radiation transmissive material and having a working region adapted to contact tissue to be treated, the working region of the tip including sidewalls, said tip having a bore therein for receiving said output end of said optical fiber, said output end being at least partially surrounded by said laser radiation transmissive material, said output end of said optical fiber being spaced from said laser radiation transmissive material so as to define a gap therebetween, said gap being in proximity to and in thermally-conductive relationship with said working region of said tip so that heat energy generated at the gap significantly raises the temperature of the working region of said tip, said gap being sufficiently distant from the working region of said tip so as to allow at least a portion of the beam of laser radiation to strike the sidewalls an first locations, reflect back into the tip and exit the tip at second locations different from the first locations.

* * * * *